(12) United States Patent
Okada et al.

(10) Patent No.: US 6,278,267 B1
(45) Date of Patent: Aug. 21, 2001

(54) METHOD OF DETERMINING IMPURITY CONTENT AND APPARATUS FOR THE SAME

(75) Inventors: Hiroshi Okada; Sadao Hirae; Motohiro Kono, all of Kyoto (JP)

(73) Assignee: Dainippon Screen Mfg. Co., Ltd. (JP)

( * ) Notice: Subject to any disclaimer, the term of this patent is extended or adjusted under 35 U.S.C. 154(b) by 0 days.

(21) Appl. No.: 09/134,584

(22) Filed: Aug. 14, 1998

(30) Foreign Application Priority Data

Aug. 20, 1997 (JP) .................................................. 9-240339
Apr. 27, 1998 (JP) ................................................. 10-134587

(51) Int. Cl.[7] ........................ G01N 27/00; G01R 31/308; G01R 31/311
(52) U.S. Cl. ........................ 324/71.5; 324/501; 324/551; 324/752; 324/765
(58) Field of Search .................................... 324/501, 537, 324/750, 752, 765, 766, 551, 554, 659, 672, 679, 71.5

(56) References Cited

U.S. PATENT DOCUMENTS

| | | | |
|---|---|---|---|
| H111 | * 8/1986 | Flesner | 324/766 |
| 3,995,216 | * 11/1976 | Yun | 324/765 |
| 5,225,690 | 7/1993 | Sakai et al. | 250/261 |
| 5,760,594 | * 6/1998 | Lee | 324/663 |

FOREIGN PATENT DOCUMENTS

| | | |
|---|---|---|
| 4-328842 | 11/1992 | (JP) . |
| 5-335393 | 12/1993 | (JP) . |
| 9-199383 | 7/1997 | (JP) . |

OTHER PUBLICATIONS

M. Itsumi, et al., "Effect of UV Light Irradiation on Passivation of Nobile Ions in MOS Devices", *The Institute Of Electronics, Information And Communication Engineers*, SDM97–94 (Aug. 1997), pp. 13–20.

R. Williams, "Photoemission of Electronics from Silicon into Silicon Dioxide", Physical Review, vol. 140, number 2A, Oct. 1965, pp. A 569–575.

* cited by examiner

*Primary Examiner*—Glenn W. Brown
(74) *Attorney, Agent, or Firm*—Ostrolenk, Faber, Gerb & Soffen, LLP

(57) ABSTRACT

The method obtains a first C-V curve prior to irradiation with light and a second C-V curve after the irradiation with light. The method determines the amount of the intra-film impurity ions in an insulating film in the state prior to the irradiation with light, based on the first and the second C-V curves.

7 Claims, 10 Drawing Sheets

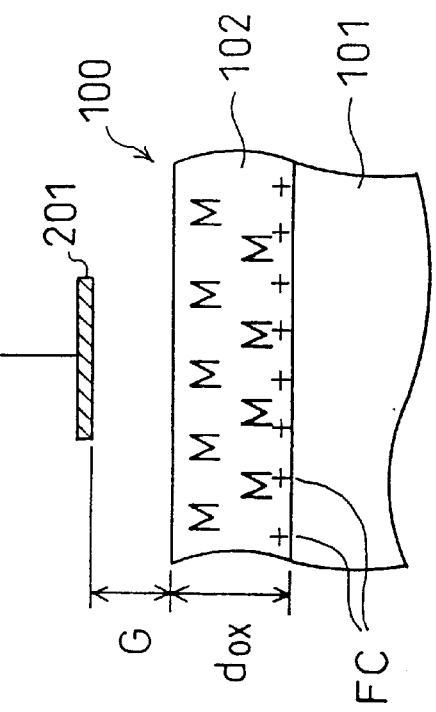
Fig. 3(A-1) BEFORE IRRADIATION WITH LIGHT
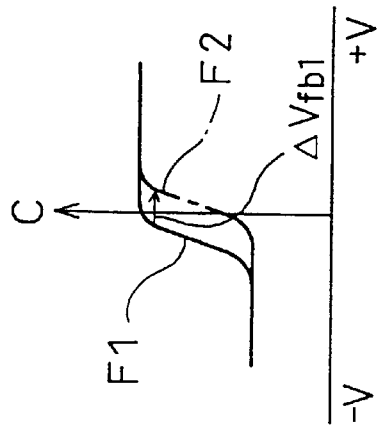
Fig. 3(A-2)
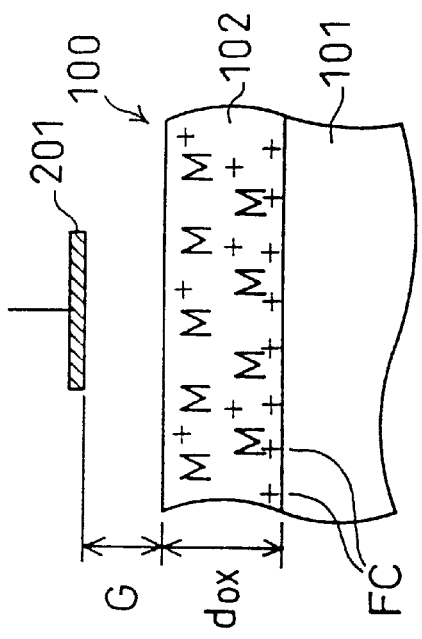
Fig. 3(B-1) AFTER IRRADIATION WITH LIGHT
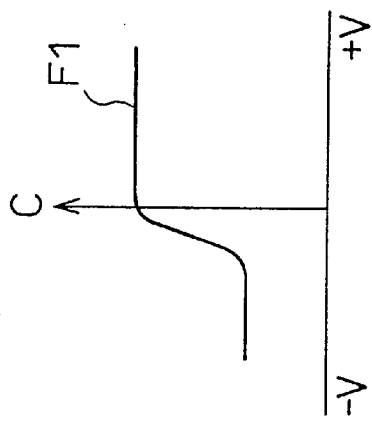
Fig. 3(B-2)

Fig. 8(A) AFTER IRRADIATION
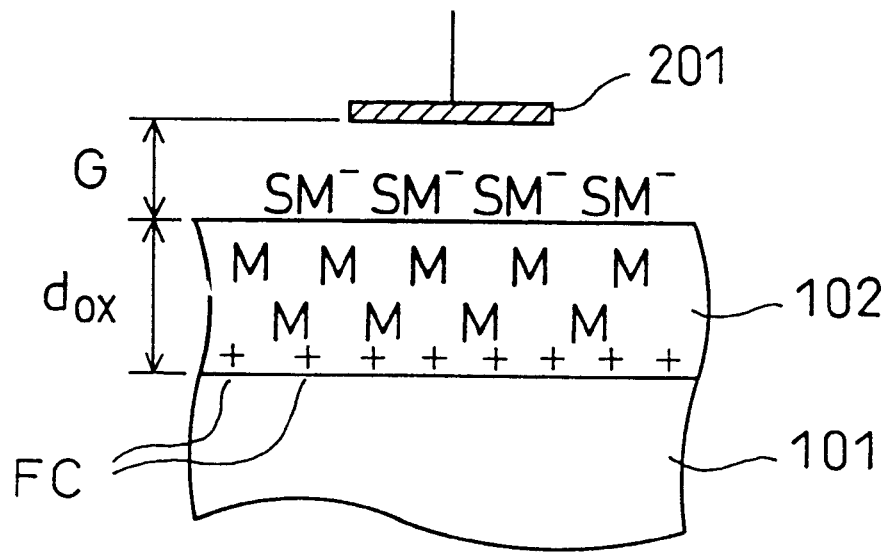
Fig. 8(B)
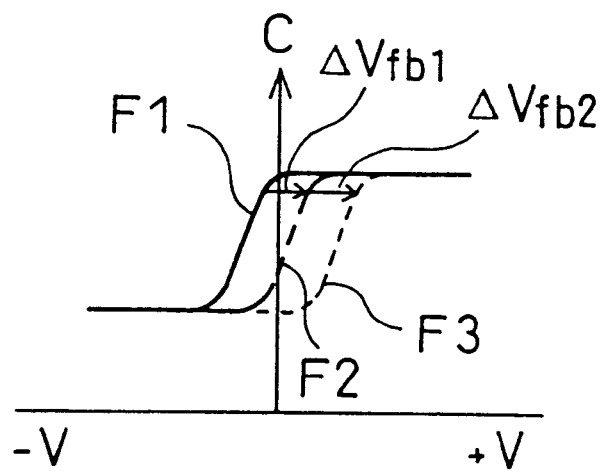

METHOD OF DETERMINING IMPURITY CONTENT AND APPARATUS FOR THE SAME

BACKGROUND OF THE INVENTION

1. Field of the Invention

The present invention relates to a technique that determines the amount of impurities present in the vicinity of an insulating film formed on surface of a substrate.

2. Description of the Related Art

An insulating film formed on a surface of a substrate, such as a semiconductor wafer, is often contaminated with mobile ions including alkali metal ions (hereinafter referred to as 'intra-film impurity ions') in the course of wafer processing. These intra-film impurity ions readily move under the influence of an electric field and thereby lower the stability of electric characteristics of the surface of the semiconductor wafer.

The amount of intra-film impurity ions in the insulating film is generally measured by C-V characteristic measurement with the aid of BT (bias temperature) treatment. In the BT treatment, a direct current bias is applied to a gate electrode on the insulating film at high temperatures.

The BT treatment heats up the semiconductor wafer to high temperatures and thereby requires a relatively long treatment time.

SUMMARY OF THE INVENTION

Accordingly, an object of the present invention is to provide a technique that determines the amount of impurity ions present in the vicinity of an insulating film formed on surface of a substrate, such as a semiconductor wafer, without heating the substrate.

The above and other objects of the invention are attained at least partly by a method of determining an amount of impurities in the vicinity of an insulating film formed on a surface of a substrate. The method comprises the steps of: (a) obtaining a first measurement value of a predetermined electrical property, which relates to an amount of intra-film impurity ions in the insulating film; (b) irradiating the surface of the substrate with light of a first wavelength range, so as to electrically neutralize the intra-film impurity ions; (c) obtaining a second measurement value of the predetermined electrical property in the state that the intra-film impurity ions are neutralized; and (d) determining the amount of the intra-film impurity ion in a state prior to the irradiation with the light of the first wavelength range, based on the first measurement value and the second measurement value.

Irradiation of the surface of the substrate with light of the specified first wavelength range electrically neutralizes the intra-film impurity ions in the insulating film. The method can determine the amount of the intra-film impurity ions in the state prior to the irradiation with the light, based on the measurement values of the predetermined electrical property, which relates to the amount of the intra-film impurity ion in the insulating film, obtained before and after the irradiation with the light.

In a preferred embodiment of the invention, the insulating film contains plural kinds of intra-film impurity ions, and the first wavelength range comprises a specific wavelength range that electrically neutralize one specific kind of intra-film impurity ions among the plural kinds of different intra-film impurity ions and does not electrically neutralize the other kinds of the intra-film impurity ions.

This structure enables the amount of one specific intra-film impurity ion in the insulating film to be determined separately from the other intra-film impurity ions.

In a preferred embodiment of the invention, the first wavelength range is at least part of a range of about 100 nm to about 500 nm.

Irradiation with the light of this wavelength range can effectively neutralize the intra-film impurity ions in the step (b).

In a preferred embodiment of the invention, the light of first wavelength range does not ionize impurities adsorbed to the surface of the insulating film.

If the adsorbed impurities are present on the surface of the insulating film, inappropriate irradiation would ionize the adsorbed impurities while neutralizing the intra-film impurity ion in the insulating film. This would make it difficult to accurately determine the amount of the intra-film impurity ions in the step (d). In such cases, appropriate irradiation with light of the specific wavelength range, which neutralizes only the intra-film impurity ions but does not ionize the adsorbed impurities, enables accurate determination of the amount of the intra-film impurity ions.

In a preferred embodiment of the invention, the method further comprises the steps of: (e) irradiating the surface of the substrate with light of a second wavelength range, which includes a range different from the first wavelength range, so as to ionize the adsorbed impurities; (f) obtaining a third measurement value of the predetermined electrical property in the state that the adsorbed impurities are ionized; and (g) determining an amount of the adsorbed impurities in a state prior to the irradiation with the light of the second wavelength range, based on the second measurement value and the third measurement value.

The adsorbed impurities on the surface of the insulating film are ionized in the step (e), while the intra-film impurity ions are neutralized in the step (b). The amount of the adsorbed impurities is then determined in the step (g).

In a preferred embodiment of the invention, the first wavelength range is at least part of a range of about 270 nm to about 300 nm, and the second wavelength range is at least part of a range of about 250 nm to about 270 nm.

Irradiation with the light of the first wavelength range in the step (b) effectively neutralizes only the intra-film impurity ions when adsorbed impurities are present on the surface of the insulating film. This enables the amount of the intra-film impurity ions to be determined accurately in the step (d). Irradiation with the light of the second wavelength range in the step (e) effectively ionizes the adsorbed impurities. This enables the amount of the adsorbed impurities to be determined accurately in the step (g).

The present invention is also directed to an impurity content determination apparatus for determining an amount of impurities in the vicinity of an insulating film formed on surface of a substrate. The impurity content determination apparatus comprises: an electrical property measurement unit that specifies a measurement value of a predetermined electrical property, which relates to the amount of impurities in the vicinity of the insulating film; a first irradiation unit that irradiates the surface of the substrate with light of a first wavelength range, which electrically neutralizes intra-film impurity ions included in the insulating film; and an intra-film impurity ion content determination unit that determines an amount of the intra-film impurity ions in a state prior to the irradiation with the light of the first wavelength range, based on a first measurement value of the predetermined electrical property in the state prior to the irradiation with the light of the first wavelength range and a second measurement value of the predetermined electrical property in a state after the irradiation with the light of the first wavelength range.

These and other objects, features, aspects, and advantages of the present invention will become more apparent from the following detailed description of the preferred embodiments with the accompanying drawings.

BRIEF DESCRIPTION OF THE DRAWINGS

FIGS. 3(A-1),3(A-2),3(B-1) and 3(B-2) show a method of determining the amount of intra-film impurity ions in the first embodiment;

FIGS. 8(A) and 8(B) show a method of determining the amount of the adsorbed impurities in the second embodiment;

DESCRIPTION OF THE PREFERRED EMBODIMENTS

Figure 1:
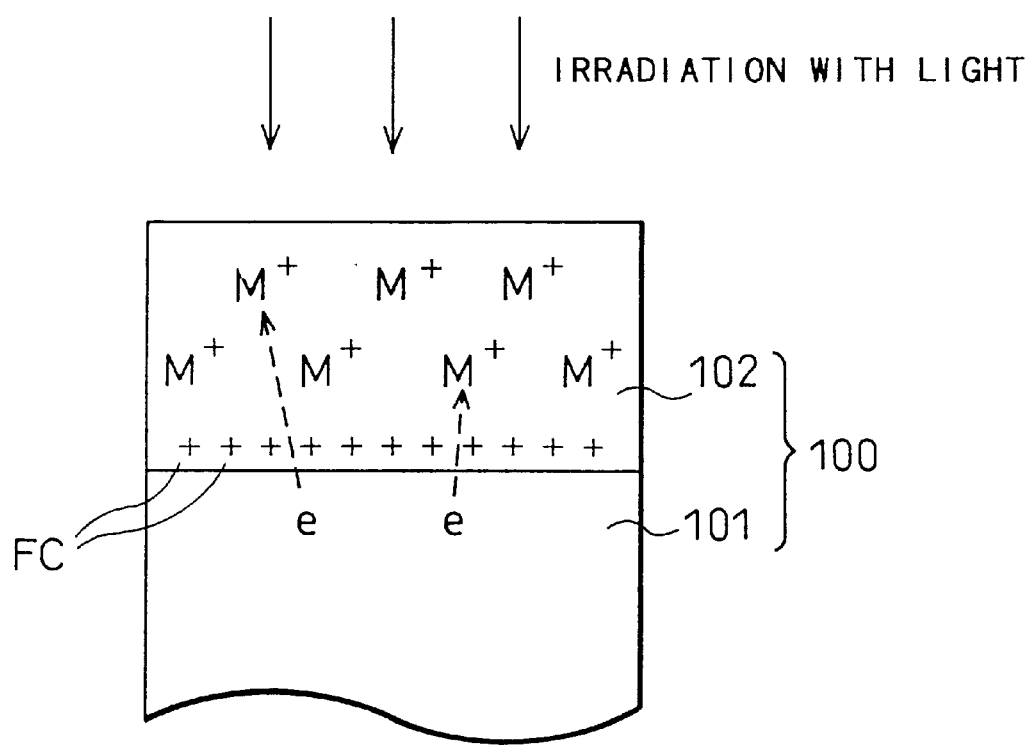
FIG. 1 schematically illustrates a cross section of surface part of a semiconductor wafer, which is an object to be measured in a first embodiment according to the present invention.

A. First Embodiment:

FIG. 1 illustrates schematically illustrates a cross section of surface part of a semiconductor wafer, which is an object to be measured in a first embodiment. A semiconductor wafer 100 comprises a substrate 101 and an insulating film 102 formed on the substrate 101. Fixed electric charges FC are present in the vicinity of an interface between the insulating film 102 and the semiconductor substrate 101, and intra-film impurity ions $M^+$ are present in the insulating film 102. The letter 'M' written in the insulating film 102 represents impurity elements and '$M^{+}$' represents positive ions of the impurity elements.

The insulating film 102 is contaminated with the intra-film impurity ions $M^+$ shown in FIG. 1 mainly in the process of forming the insulating film 102 on the semiconductor wafer 101. A variety of intra-film impurity ions (such as Na, Li, Fe, Ni, Cu, Zn, and Al) may be included in the insulating film 102.

When the semiconductor wafer 100 is irradiated with specific light, the light transmits through the insulating film 102 and reaches the semiconductor substrate 101. Electrons inside the substrate 101 receive energy from the light and jump into the insulating film 102 to electrically neutralize the intra-film impurity ions $M^+$ (FIG. 1) in the insulating film 102.

The first embodiment determines the amount of the intra-film impurity ions $M^+$ while taking advantage of the fact that the intra-film impurity ions $M^+$ irradiated with light are electrically neutralized. The fixed electric charges FC shown in FIG. 1 are not affected by the light as will be discussed later.

Figure 2:
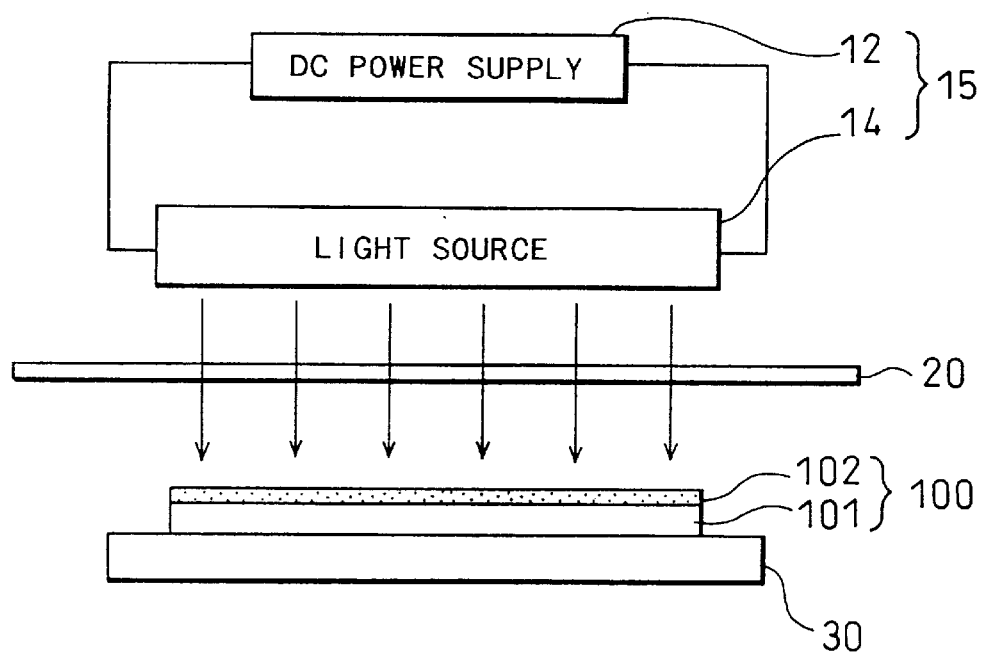
FIG. 2 illustrates the structure of an irradiation device used in the first embodiment of the present invention.

FIG. 2 illustrates the structure of an irradiation device used in the first embodiment of the present invention. The irradiation device has a light source unit 15, which includes a direct current power supply 12 and a light source 14, an optical filter 20, and a stage 30 on which the semiconductor wafer 100 is mounted. The light source 14 is, for example, a high-pressure mercury lamp having outputs of 3 to 4 W and emits light of a wavelength range of about 200 to 600 nm. Only the light component of a specific wavelength range out of the emitted light transmits through the optical filter 20 and irradiates the surface of the semiconductor wafer 100.

As mentioned above, the variety of intra-film impurity ions (such as Na, Li, Fe, Ni, Cu, Zn, and Al) may be included in the insulating film 102 of the semiconductor wafer 100. The wavelength range of light, with which the semiconductor wafer 100 is irradiated (that is, the transmission characteristics of the optical filter 20) depends upon the type of the intra-film impurity ion to be neutralized. The relationship between the kind of the intra-film impurity ion and the wavelength range of light suitable for neutralization of the intra-film impurity ion can be determined experimentally. By way of example, a typical experiment irradiates the insulating film 102 with light of a single wavelength, and determines whether or not a specific intra-film impurity ion is neutralized. This determines the wavelength range of light suitable for neutralization of each intra-film impurity ion. The experiments performed by the inventors of the present invention have shown that an UV ray (ultraviolet ray) in the wavelength range of about 155 nm to about 384 nm, especially the UV ray in the wavelength range of about 200 nm to about 300 nm, is suitable for neutralization of $Na^+$ included in an SiO2 film formed on surface of a silicone substrate. Light in the wavelength range of about 100 nm to about 500 nm is suitable for neutralizing the variety of intra-film impurity ions.

Figure 4:
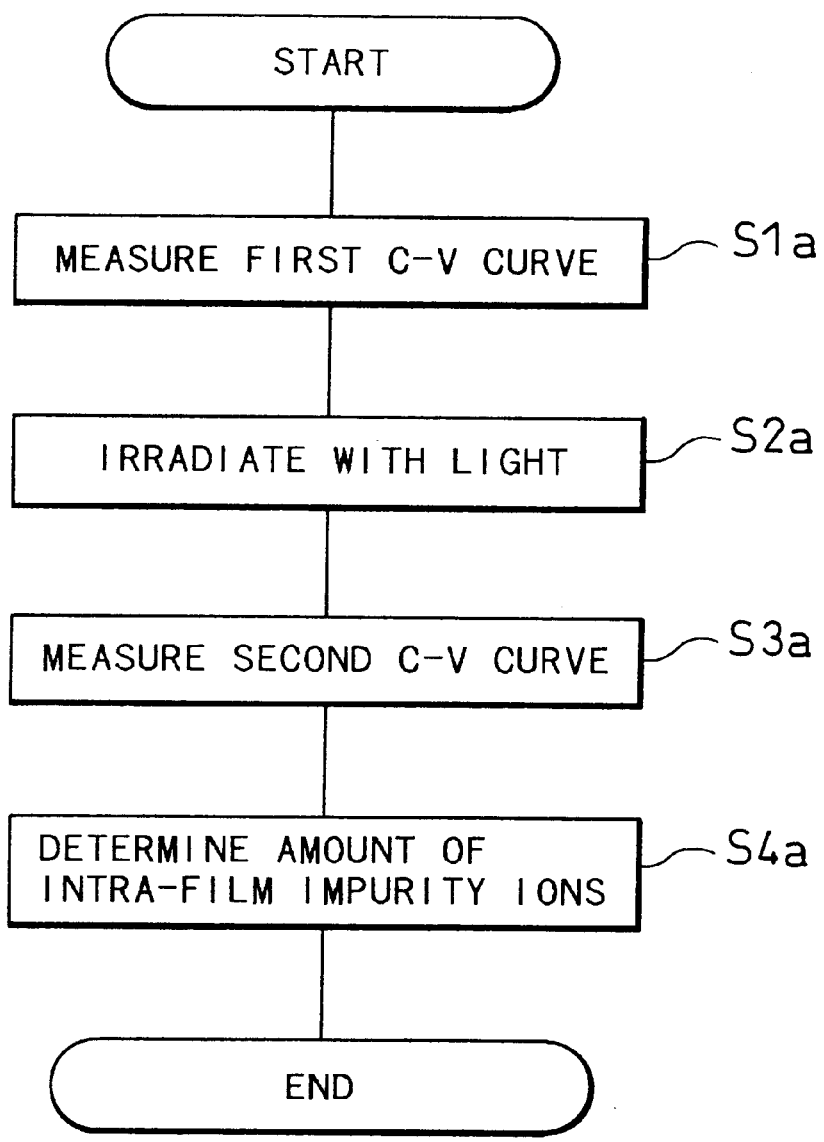
FIG. 4 is a flowchart showing a procedure of determining the amount of the intra-film impurity ions executed in the first embodiment.

FIGS. 3(A-1),3(A-2),3(B-1) and 3(B-2) show a method of determining the amount of intra-film impurity ions in the first embodiment. FIG. 4 is a flowchart showing a procedure of determining the amount of the intra-film impurity ions executed in the first embodiment. At step S1$a$, a non-contact C-V measurement of the semiconductor wafer 100 is carried out to obtain a first C-V curve, prior to irradiation with light. A non-contact type C-V measurement device used here positions a measurement electrode 201 across a gap above the semiconductor wafer 100 and carries out the C-V measurement in this state. The structure of the non-contact type C-V measurement device and its measurement method are described in U.S. Pat. No. 5,225,690 and JAPANESE PATENT LAID-OPEN GAZETTE No. 4-328842, the disclosure of which is herein incorporated by reference (for all purposes). The non-contact type C-V measurement device acts as an electrical property measurement unit of the present invention.

FIG. 3(A-1) shows a state in which a measurement electrode 201 is positioned across a gap G of about 350 angstrom above the surface of the semiconductor wafer 100 in the non-contact type C-V measurement device. In a thermal equilibrium state at room temperature, it is considered that only part of the impurity elements included in the insulating film 102 are ionized. The fixed electric charges FC are present in the vicinity of the interface between the substrate 101 and the insulating film 102.

FIG. 3(A-2) is a graph showing a first C-V curve F1 obtained at step S1a. In the C-V measurement the gap G is measured between the measurement electrode 201 and the surface of the semiconductor wafer 100 (see FIG. 3(A-1)). A thickness $d_{ox}$ of the insulating film 102 is known to be a design value preset in the forming process of the insulating film 102.

At step S2a in the flowchart of FIG. 4, the surface of the semiconductor wafer 100 is irradiated with the light in the ultraviolet wavelength range emitted from the irradiation device shown in FIG. 2. The insulating film 102 has the extremely small thickness of about 100 to 1000 angstrom and is thereby regarded as substantially transparent with respect to the light in the ultraviolet wavelength range. The intra-film impurity ions $M^+$ included in the insulating film 102 are therefore sufficiently irradiated with the light. FIG. 3(B-1) shows a state in which substantially all the intra-film impurity ions $M^+$ included in the insulating film 102 are neutralized by the irradiation.

After the irradiation, the method carries out a second C-V measurement at step S3a. FIG. 3(B-2) shows a second C-V curve F2 thus obtained together with the first C-V curve F1. The first C-V curve F1 represents the result of the measurement in the state where the intra-film impurity ions $M^+$ are present in the insulating film 102, whereas the second C-V curve F2 represents the result of the measurement in the state where substantially all the intra-film impurity ions $M^+$ in the insulating film 102 have been neutralized. When the intra-film impurity ions $M^+$ are arbitrarily distributed in the insulating film 102, a flat band voltage shift $\Delta Vfb1$ from the first C-V curve F1 to the second C-V curve F2 is expressed as Equations (1a)–(1c) given below:

$$\Delta Vfb_1 = -\frac{qN_0}{\varepsilon_0}\left(G + \frac{\bar{x}}{\varepsilon_{ox}}\right) \quad (1a)$$

$$qN_0 = \int_0^{dox} P_0(x)\,dx \quad (1b)$$

$$\bar{x} = \frac{\int_0^{dox} x \cdot P_0(x)\,dx}{\int_0^{dox} P_0(x)\,dx} \quad (1c)$$

where $\varepsilon_0$ denotes a dielectric constant in vacuum; $\varepsilon_{ox}$ a relative dielectric constant of the insulating film 102; $P_0(x)$ a spatial density distribution of the intra-film impurity ions (/cm³) when the origin of the coordinate x is set on the interface between the air and the insulating film 102 and the substrate is put on the positive side of the x axis; G a gap between the insulating film 102 and the measurement electrode 201; and $d_{ox}$ a thickness of the insulating film 102.

In Equations (1a)–(1c), the values other than the density distribution $P_0(x)$ of the intra-film impurity ions are known. The spatial distribution $P_0(x)$ is thus determined from the flat band voltage shift $\Delta Vfb1$ by numerical analysis. An amount $N_0$ of the intra-film impurity ions is then obtained from the distribution $P_0(x)$. An intra-film impurity ion content determination unit implemented by a computer (not shown) performs the calculation according to Equations (1a)–(1c) and determines the amount $N_0$ of the intra-film impurity ions at step S4a in the flowchart of FIG. 4.

Figure 5:
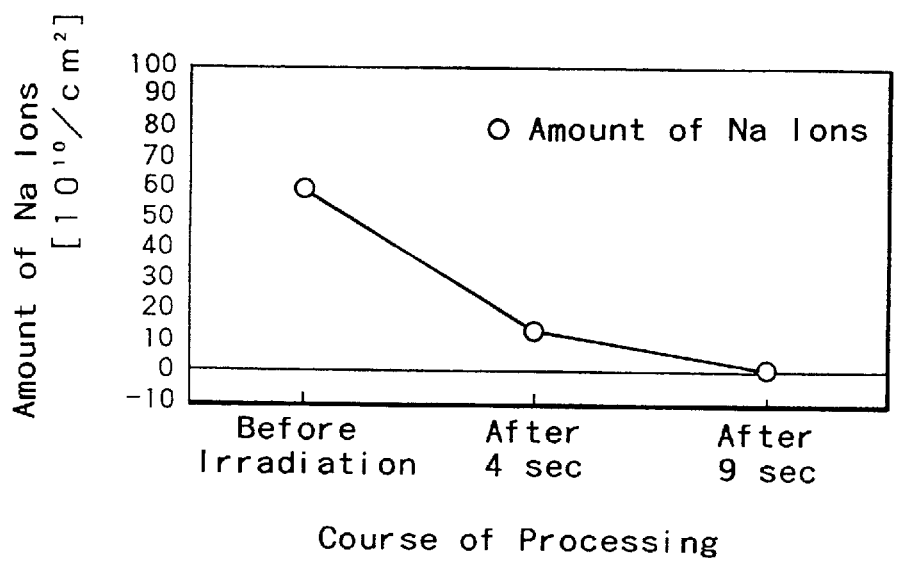
FIG. 5 is a graph showing results of an experiment that irradiates the surface of the semiconductor wafer with light to neutralize the intra-film impurity ions.

FIG. 5 is a graph showing results of an experiment that irradiates the surface of the semiconductor wafer with light to neutralize the intra-film impurity ions. The method of the experiment first injected $60 \times 10^{10}/cm^2$ of Na ion ($Na^+$), which is a typical intra-film impurity ion, into the insulating film. The method then irradiated the semiconductor wafer for approximately 4 seconds with light in the wavelength range of 200 to 600 nm emitted from the high-pressure mercury lamp having the outputs of about 3 to 4 W, and measured the amount of Na ions in the insulating film. The measurement was based on the flat band voltage difference $\Delta Vfb1$ between the C-V curve of the semiconductor wafer that was free from Na ions and the C-V curve of the semiconductor wafer after injection of Na ions and irradiation with light for 4 seconds. The semiconductor wafer was further irradiated with the light for about 5 seconds, and the amount of Na ions in the insulating film was measured again. The result of measurement is given as 'after 9 sec' in the graph of FIG. 5. As clearly understood from the results, when the semiconductor wafer was irradiated with light for about 9 seconds, substantially all the Na ions in the insulating film were neutralized.

It was originally expected that irradiation with light would ionize the impurity elements M when a positive bias voltage was applied to the rear face of the substrate 101 (that is, the stage 30 in FIG. 2) and that irradiation with light would neutralize the intra-film impurity ions $M^+$ when a negative bias voltage was applied to the rear face of the substrate 101. The inventors of the present invention, however, found that irradiation with light neutralizes the intra-film impurity ions $M^+$ n the insulating film 102 irrespective of the bias voltage.

As shown in FIG. 3(A-1), the fixed electric charges FC are present in the vicinity of the interface between the insulating film 102 and the substrate 101. It has been confirmed experimentally that these fixed electric charges FC are hardly changed by irradiation with light. The inventors injected $68.5 \times 10^{10}/cm^2$ of the fixed electric charges in the vicinity of the interface between the insulating film 102, which was free from the intra-film impurity ions, and the substrate 101, and irradiated the wafer with light for about 60 seconds. The light of irradiation was identical with that used for neutralization of Na ions (that is, the light in the wavelength range of 200 to 600 nm emitted from the high-pressure mercury lamp having the outputs of 3 to 4 W). The amount of the fixed electric charges measured after the irradiation was $69.0 \times 10^{10}/cm^2$, which was substantially equal to the value before the irradiation. These results show that the irradiation neutralizes the intra-film impurity ions in the insulating film 102 while causing substantially no change of the fixed electric charges in the vicinity of the interface of the insulating film 102.

Irradiation of the semiconductor wafer with light in the specific wavelength range neutralizes the intra-film impurity ions in the insulating film without affecting the fixed electric charges FC in the vicinity of the interface of the insulating film. Measurement of the C-V curves before and after the irradiation thus determines the amount $N_0$ of the intra-film impurity ions in the insulating film at a high accuracy. The measurement steps of FIG. 4 are all carried out at room temperature, and do not require the semiconductor wafer 100 to be heated unlike the BT treatment. The irradiation requires a relatively short time period, which is in the range of several seconds to several tens seconds. The whole processing time required for determining the amount of the intra-film impurity ions is accordingly shortened, compared with the conventional method.

If the wavelength range of the light is set to be suitable for neutralizing only a specific kind of the intra-film impurity ions, the amount of the specific kind of the intra-film impurity ions can be measured separately of the other of the intra-film impurity ions. Especially in the first embodiment, the specific wavelength range is selected simply by changing the optical filter 20. This enables the light of the specific wavelength range to be obtained at a relatively low cost.

Since the first embodiment carries out the C-V measurement with the non-contact type C-V measurement device, there is no fear of the contamination on the surface of the semiconductor wafer, which is a significant problem with a contact type measurement device.

Figure 6:
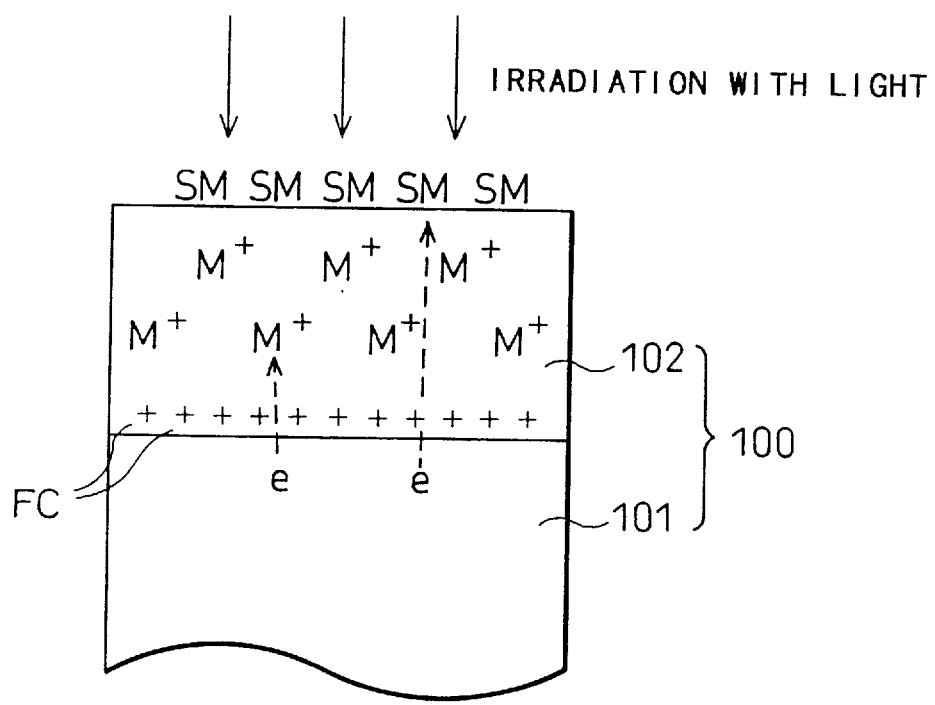
FIG. 6 schematically illustrates a cross section of surface part of a semiconductor wafer, which is an object to be measured in a second embodiment according to the present invention.

B. Second Embodiment:

FIG. 6 schematically illustrates a cross section of surface part of a semiconductor wafer, which is an object to be measured in a second embodiment according to the present invention. Like the state shown in FIG. 1, fixed electric charges FC are present in the vicinity of an interface between the insulating film 102 and the semiconductor substrate 101, whereas intra-film impurity ions $M^+$ are present in the insulating film 102. The surface of the insulating film 102 is contaminated with adsorbed impurities SM. The adsorbed impurities SM are mainly organic substances and adhere to the surface of the insulating film 102, for example, during storage of the semiconductor wafer 100.

When the semiconductor wafer 100 is irradiated with specific light, the electrons in the semiconductor wafer 101 jump into the insulating film 102 to neutralize the intra-film impurity ions $M^+$ in the insulating film 102 (see FIG. 6).

The electrons in the semiconductor substrate 101 that receive higher energy from the light reach the surface of the insulating film 102. When the adsorbed impurities SM are present on the surface of the insulating film 102 as shown in FIG. 6, the electrons convert the adsorbed impurities SM into negative ions.

The present invention takes advantage of the fact that the irradiation neutralizes the intra-film impurity ions $M^+$ and ionizes the adsorbed impurities SM to negative ions, in order to determine the amounts of the intra-film impurity ions and the adsorbed impurities. The fixed electric charges FC are not affected by the irradiation as described previously.

Figure 7:
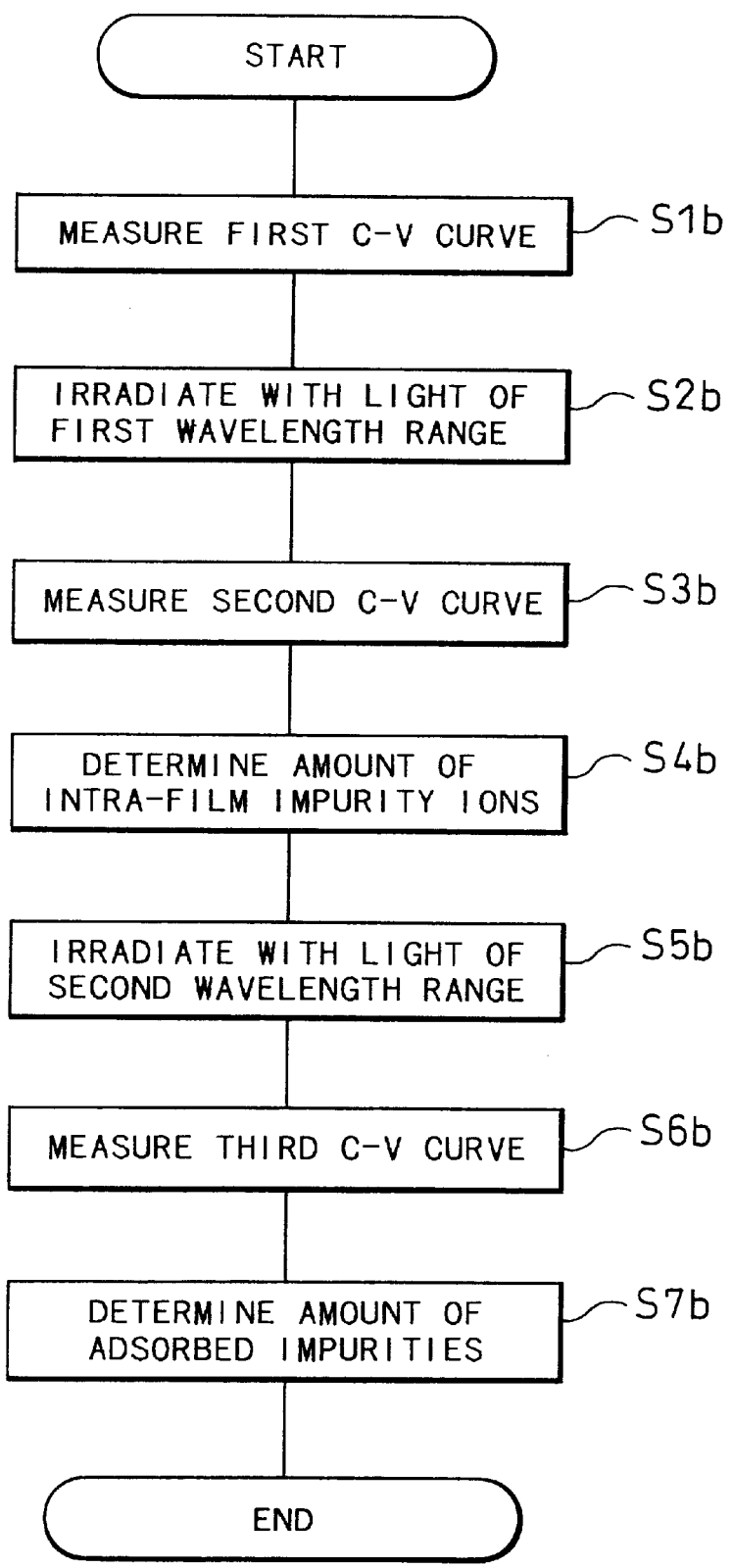
FIG. 7 is a flowchart showing a procedure of determining the amount of the intra-film impurity ions and the amount of adsorbed impurities executed in the second embodiment.

FIG. 7 is a flowchart showing a procedure of determining the amount of the intra-film impurity ions and the amount of the adsorbed impurities. The steps S1b through S4b are identical with those shown in FIG. 4. Since the adsorbed impurities SM are present on the surface of the insulating film 102 in the second embodiment as shown in FIG. 6, the light emitted from the irradiation device shown in FIG. 2 at step S2b is thus restricted to have a specific wavelength range. If the semiconductor wafer is irradiated with light of an inappropriate wavelength range at step S2b, the intra-film impurity ions $M^+$ in the insulating film 102 are neutralized while the adsorbed impurities SM on the surface of the insulating film 102 are ionized. This may result in inaccurate determination of the amount of the intra-film impurity ions $M^+$. It is accordingly required to irradiate the semiconductor wafer with light of an appropriate wavelength range that does not ionize the adsorbed impurities SM.

The inventors of the present invention have found that adsorbed impurities SM on an $SiO_2$ film formed on a silicon substrate are ionized by an UV ray in the wavelength range of not greater than about 270 nm. The suitable wavelength range of the light at step S2b, (hereinafter referred to as the 'first wavelength range') is thus not less than about 270 nm. The light of this specific wavelength range neutralizes various types of the intra-film impurity ions without ionizing the adsorbed impurities SM. The favorable first wavelength range is about 270 nm to about 300 nm, which neutralizes all the intra-film impurity ions within a short time period.

Irradiation with the light of the specific wavelength range enables only the amount $N_0$ of the intra-film impurity ions existing in the insulating film 102 to be determined at step S4b, even when the adsorbed impurities are present on the surface of the insulating film 102.

At step S5b in the flowchart of FIG. 7, the semiconductor wafer is further irradiated with light of a second wavelength range emitted from the irradiation device shown in FIG. 2, while the intra-film impurity ions $M^+$ are all neutralized. The suitable second wavelength range is not greater than about 270 nm that ionizes the adsorbed impurities on the surface of the insulating film. Irradiation with a UV ray of not greater than about 270 nm enables the electrons in the semiconductor wafer 101 to reach the surface of the insulating film 102 to ionize the adsorbed impurities SM on the surface of the insulating film 102. The preferable second wavelength range is about 250 nm to about 270 mn that causes less damages on the substrate.

FIGS. 8(A) and 8(B) show a method of determining the amount of the adsorbed impurities in the second embodiment. FIG. 8(A) shows a state in which irradiation with light has ionized substantially all the adsorbed impurities SM on the surface of the insulating film 102.

After the irradiation, the method carries out a third C-V measurement at step S6b in the flowchart of FIG. 7. FIG. 8(B) is a graph showing a third C-V curve F3 thus obtained together with the first C-V curve F1 and the second C-V curve F2 respectively obtained at steps S1b and S3b. The first and the second C-V curves F1 and F2 represent the results of the measurement in the state where the adsorbed impurities SM on the surface of the insulating film 102 are not ionized, whereas the third C-V curve F3 represents the result of the measurement in the state where substantially all the adsorbed impurities SM are ionized to negative ions. The ionized adsorbed impurities $SM^-$ are localized on the surface of the insulating film 102. A flat band voltage shift $\Delta Vfb2$ from the second C-V curve F2 to the third C-V curve F3 is thus expressed as Equation (2) given below:

$$\Delta Vfb_2 = -\frac{qN_s}{\varepsilon_0} \cdot G \qquad (2)$$

where $N_s$ denotes an amount of adsorbed impurities, and G denotes a gap between the measurement electrode 201 and the surface of the insulating film 102. The shift $\Delta Vfb2$ is known from the results of the measurements at steps S4b and S6b, so that the amount $N_s$ of the adsorbed impurities is calculated according to Equation (2). An adsorbed impurity content determination unit implemented by the computer (not shown) determines the amount $N_s$ of the adsorbed impurities at step S7b (in the flowchart of FIG. 7).

As described above, the first irradiation with light of the first wavelength range neutralizes only the intra-film impurity ions in the insulating film, and the second irradiation with light of the second wavelength range ionizes the adsorbed impurities on the surface of the insulating film. Measurement of the C-V curves before and after the first irradiation with light of the first wavelength range and before and after the second irradiation with light of the second wavelength range accordingly determines the amount of the intra-film impurity ions in the insulating film and the amount of the adsorbed impurities on the surface of the insulating film with high accuracy.

As clearly understood from the above description, the light source unit 15 and the optical filter 20 shown in FIG. 2 acts as the first and second irradiation units of the present invention.

Figure 9:
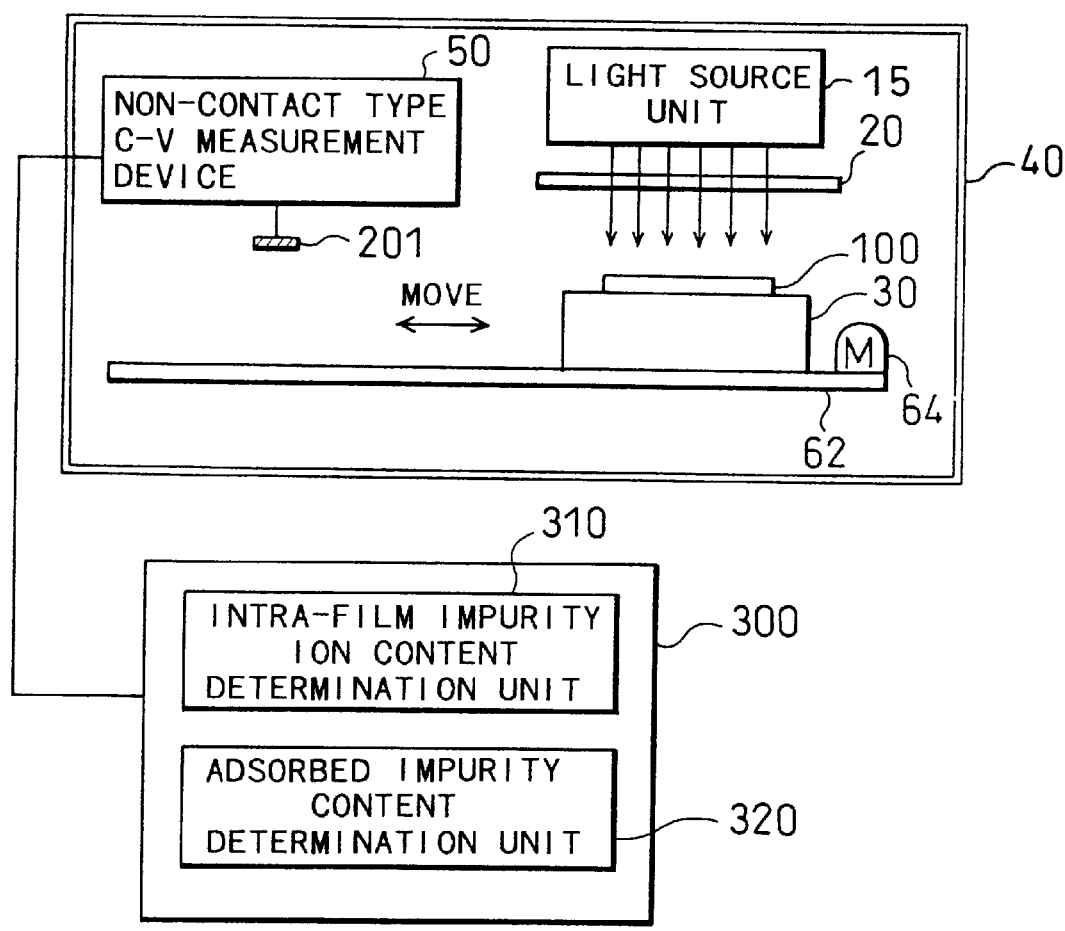
FIG. 9 illustrates the structure of an impurity content determination apparatus as a third embodiment according to the present invention.

C. Third Embodiment:

FIG. 9 illustrates the structure of an impurity content determination apparatus as a third embodiment according to the present invention. A measurement section of the impurity content determination apparatus is accommodated in a casing 40. The constituents included in the casing 40 include a light source unit 15, an optical filter 20, a stage 30, a non-contact type C-V measurement device 50 having a measurement electrode 201, a rail 62 that enables the stage 30 to shift in the horizontal direction, and a motor 64 that moves the stage 30 along the rail 62.

The non-contact type C-V measurement device 50 has a fundamental structure that is similar to that of the non-contact type C-V measurement device disclosed in JAPANESE PATENT LAID OPEN GAZETTE No. 4-328842 described previously. The non-contact type C-V measurement device 50 is connected with a computer 300. The computer 300 includes an intra-film impurity ion content determination unit 310 and an adsorbed impurity content determination unit 320. The intra-film impurity ion content determination unit 310 determines the amount $N_0$ of the intra-film impurity ions, whereas the adsorbed impurity content determination unit 320 determines the amount $N_s$ of the adsorbed impurities.

The casing 40 has a sealed dust-proof structure and prevents dust from adhering to the surface of the semiconductor wafer 100. The dust-proof structure is described in JAPANESE PATENT LAID OPEN GAZETTE No. 5-335393, the disclosure of which is herein incorporated by reference. The casing 40 may be evacuated with a vacuum pump. The sealed structure (such as the dust-proof structure or the vacuum structure) of the casing 40 effectively prevents the surface of the semiconductor wafer 100 from being contaminated with dust during measurement. It may be preferable to provide an inert gas supply unit for supplying of an inert gas (for example, $N_2$) to fill the casing 40 with the inert gas. Adequate selection of the atmosphere (the type of the gas) in the casing 40 may enable the intra-film impurity ions to be electrically neutralized more efficiently.

The apparatus of the third embodiment carries out determination of the amount $N_0$ of the intra-film impurity ions in the insulating film and the amount $N_s$ of the adsorbed impurities on the surface of the insulating film according to either the procedure shown in FIG. 4 or that shown in FIG. 7. In the apparatus of the third embodiment, the semiconductor wafer 100 can be moved from the position of the irradiation with light to the position of the C-V measurement by simply shifting the stage 30 along the rail 62. This structure further shortens the whole processing time, compared with the first embodiment and the second embodiment.

It may be also preferable to dispose a small aperture after the light source unit 15. This enables only a specific position on the semiconductor wafer 100 to be irradiated with light. The amount $N_0$ of the intra-film impurity ions and the amount $N_s$ of the adsorbed impurities can thus be measured at a plurality of different positions on the wafer 100. This enables measurement of the distributions of the amount of the intra-film impurity ions and the amount of the adsorbed impurities in the vicinity of the surface of the semiconductor wafer. When the distributions of the amount of the intra-film impurity ions and the amount of the adsorbed impurities are measured, it is preferable that a two-dimensional motion mechanism is attached to the stage 30, in order to specify arbitrary positions on the surface of the wafer as the measurement positions.

Figure 10:
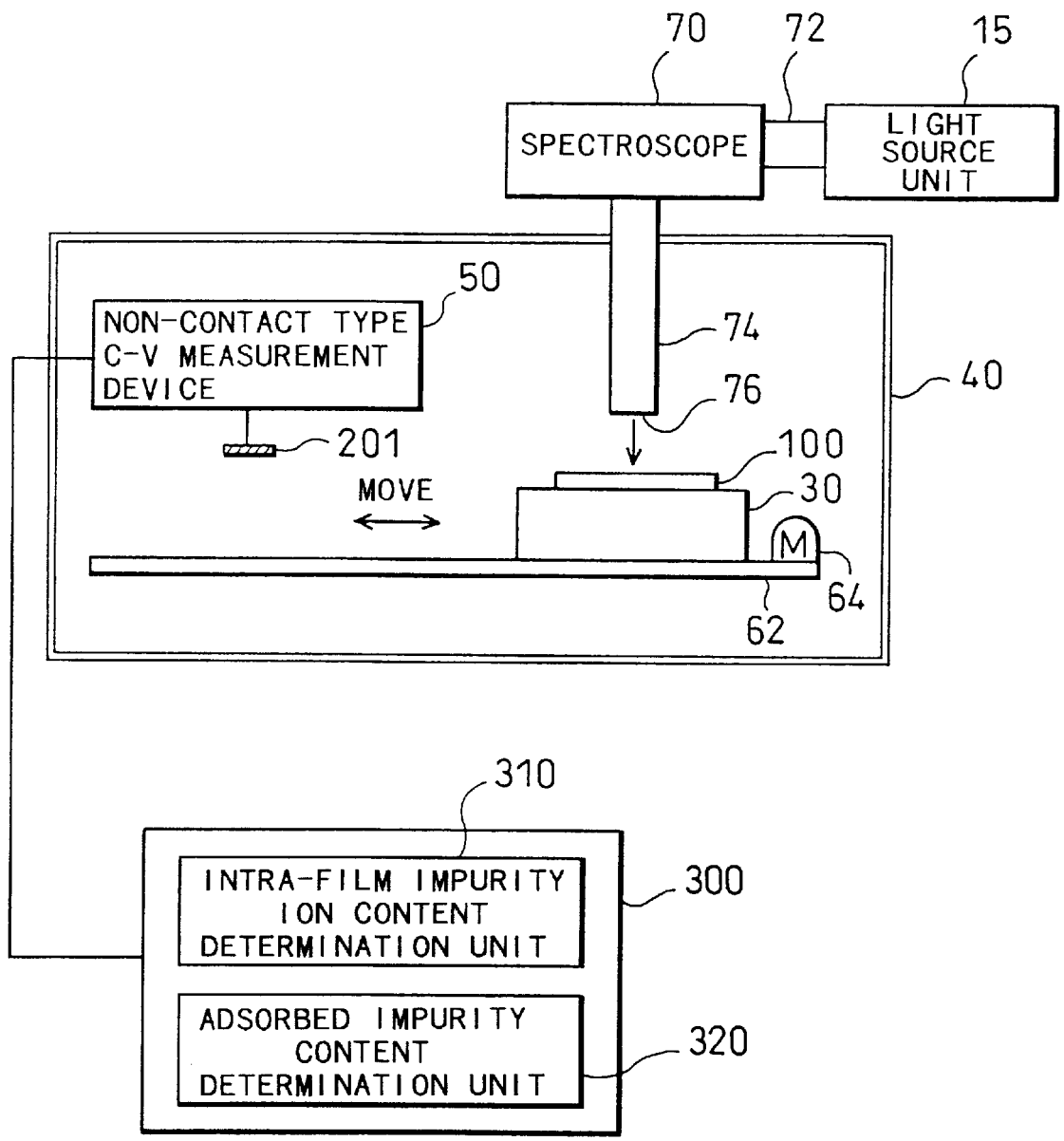
FIG. 10 illustrates the structure of another impurity content determination apparatus as a fourth embodiment according to the present invention.

D. Fourth Embodiment:

FIG. 10 illustrates the structure of another impurity content determination apparatus as a fourth embodiment according to the present invention. The impurity content determination apparatus of the fourth embodiment includes a spectroscope 70, instead of the optical filter 20 in the apparatus of the third embodiment shown in FIG. 9. Light-waveguides 72 and 74 are respectively disposed at positions between the light source unit 15 and the spectroscope 70 and below the spectroscope 70. The light source unit 15, the first light-waveguide 72, and the spectroscope 70 are placed outside the casing 40, whereas the second light-waveguide 74 is inserted into the casing 40. In the fourth embodiment, the light source unit 15, the spectroscope 70, and the light-waveguides 72 and 74 act as the first and the second irradiation units of the present invention.

Light emitted from the light source unit 15 is transmitted to the spectroscope 70 via the first light-waveguide 72. The spectroscope 70 selectively emits a light beam of a desired single wavelength. The spectroscope 70 is, for example, a grating spectroscope that utilizes a diffraction grating. Light output from the spectroscope 70 is transmitted through the second light-waveguide 74.

The light emitted from a light-emitting opening 76, which is the lower end of the second light-waveguide 74, irradiates a specific position on the semiconductor wafer 100. A two-dimensional motion mechanism (not shown) attached to the stage 30 is used to specify an arbitrary position on the surface of the semiconductor wafer 100 as the measurement position.

The apparatus of the fourth embodiment also carries out determination of the amount $N_0$ of the intra-film impurity ions in the insulating film and the amount $N_s$ of the adsorbed impurities on the surface of the insulating film according to either the procedure shown in FIG. 4 or that shown in FIG. 7. In the apparatus of the fourth embodiment, the semiconductor wafer 100 is irradiated with a light beam of a single wavelength that is suitable for electrically neutralizing a specific kind of the intra-film impurity ions by changing the settings of the spectroscope 70. If a plurality of different intra-film impurity ions are included in the insulating film, the amount of the intra-film impurity ions is measured every time when the wavelength of the light, with which the semiconductor wafer 100 is irradiated, is changed. This enables the amount of each intra-film impurity ion to be determined separately of the other intra-film impurity ions. Like the third embodiment, the fourth embodiment enables measurement of the two-dimensional distributions of the amount $N_0$ of the intra-film impurity ions and the amount $N_s$ of the adsorbed impurities in the vicinity of the surface of the semiconductor wafer.

In the above embodiments, the non-contact type C-V measurement device is used for the C-V measurement. A contact type C-V measurement device may, however, be applied for the C-V measurement. The contact type C-V measurement device that forms a measurement electrode directly on the surface of the semiconductor wafer may increase the amount of the intra-film impurity ions in the insulating film in the course of forming the measurement electrode. From this point of view, it is preferable to use the non-contact type C-V measurement device for the C-V measurement.

In the above embodiments, the flat band voltage is used to determine the amount of the intra-film impurity ions and the amount of the adsorbed impurities. Other measurement values of the C-V curve may be used for the same purpose. The C-V curve is affected to shift by the intra-film impurity ions in the insulating film and the ionized adsorbed impurities on the surface of the insulating film. By way of example, the measurement value called the 'mid-gap voltage' may be used for the determination. At the mid-gap voltage, the Fermi level coincides with the intrinsic Fermi level at the interface between the substrate and the insulating film.

In the above embodiments, the amount of the intra-film impurity ions and the amount of the adsorbed impurities are determined with the C-V curves. Instead of the C-V curve measurement, other measurement methods which measure electrical property related to the amount of the intra-film impurity ions and the amount of the ionized adsorbed impurities may be applied for the determination. For example, available methods include SPV (surface photo voltage) method and surface potential measurement method. In general, any electrical property, which relates to the amount of the intra-film impurity ions in the insulating film and the amount of the ionized adsorbed impurities on the surface of the insulating film, may be used to determine the amount of the intra-film impurity ions and the amount of the adsorbed impurities. It is, however, preferable that no shield (for example, a measurement electrode) that blocks light is present at a target position of measurement on the semiconductor wafer during irradiation with light.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of determining an amount of intra-film impurity ions in an insulating film formed on a surface of a substrate, the method comprising:
   (a) measuring an electrical property of said insulating film, thereby obtaining a first measurement;
   (b) irradiating said surface of said substrate with a first light thereby electrically neutralizing said intra-film impurity ions;
   (c) measuring said electrical property when said intra-film impurity ions are electrically neutralized by said first light, thereby obtaining a second measurement; and
   (d) determining said amount of said intra-film impurity ions in said insulating film based on said first measurement and said second measurement.

2. A method in accordance with claim 1, wherein said first light comprises a specific wavelength range that electrically neutralizes a specific type of intra-film impurity ions; and
   said first light does not electrically neutralize other types of impurities.

3. A method in accordance with claim 2, wherein said first light has a first wavelength range, and
   wherein said first wavelength range is at least part of a range of about 100 mn to about 500 mn.

4. A method in accordance with claim 1, wherein said first light does not ionize impurities adsorbed to said insulating film.

5. A method in accordance with claim 4, said method further comprising:
   (e) irradiating said surface of said substrate with a second light, said second light having a second wavelength range, and
   wherein said second wavelength range is different from said first wavelength range, and said second light ionizes impurities adsorbed in said insulating film;
   (f) measuring said electrical property when said impurities adsorbed in said insulating film are ionized by said second light, thereby obtaining a third measurement; and
   (g) determining an amount of said impurities adsorbed in said insulating film prior to said irradiation with said second light, based on said second measurement and said third measurement.

6. A method in accordance with claim 5, wherein said first wavelength range is at least part of a range of about 270 mn to about 300 nm; and
   said second wavelength range is at least part of a range of about 250 nm to about 270 mn.

7. A method in accordance with claim 6, wherein said first wavelength range comprises a wavelength range that electrically neutralizes one specific type of intra-film impurity ions in said insulating film, and
   said first light does not electrically neutralize other of said types of said intra-film impurity ions in said insulating film.

* * * * *